(12) United States Patent
Saimiya et al.

(10) Patent No.: US 10,470,990 B2
(45) Date of Patent: *Nov. 12, 2019

(54) HAIR DYE COMPOSITION

(71) Applicant: KAO CORPORATION, Chuo-ku (JP)

(72) Inventors: Hiromi Saimiya, Sumida-ku (JP);
Masaki Fukuhara, Arakawa-ku (JP);
Masayoshi Nojiri, Chiba (JP); Kyoko Kuramoto, Shinagawa-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/316,291

(22) PCT Filed: Jun. 5, 2015

(86) PCT No.: PCT/JP2015/066279
§ 371 (c)(1),
(2) Date: Dec. 5, 2016

(87) PCT Pub. No.: WO2016/186815
PCT Pub. Date: Dec. 10, 2015

(65) Prior Publication Data
US 2017/0196790 A1    Jul. 13, 2017

(30) Foreign Application Priority Data

Jun. 6, 2014  (JP) .................................. 2014-117908
Jun. 6, 2014  (JP) .................................. 2014-117909
Jun. 6, 2014  (JP) .................................. 2014-117910

(51) Int. Cl.
*A61Q 5/10* (2006.01)
*A61K 8/49* (2006.01)
*A61Q 5/06* (2006.01)

(52) U.S. Cl.
CPC ............. *A61K 8/49* (2013.01); *A61Q 5/065* (2013.01); *A61Q 5/10* (2013.01)

(58) Field of Classification Search
CPC ... A61K 8/49; A61K 8/41; A61K 8/19; A61K 8/416; A61K 2800/4324; A61K 2800/5426; A61K 2800/596; A61K 8/46; A61Q 5/10

See application file for complete search history.

(56) References Cited

U.S. PATENT DOCUMENTS 5,131,912 A  7/1992  Ehara et al.
5,393,305 A  2/1995  Cohen et al.
(Continued)

FOREIGN PATENT DOCUMENTS

CN  1105234    7/1995
CN  101820852  9/2010
(Continued)

OTHER PUBLICATIONS

STIC Search Report (U.S. Appl. No. 15/316,648) dated May 23, 2017.*

(Continued)

*Primary Examiner* — Eisa B Elhilo
(74) *Attorney, Agent, or Firm* — Oblon, McClelland, Maier & Neustadt, L.L.P.

(57) ABSTRACT

A hair dye composition comprising the following components (A), (B) and (C) and having pH (25° C.) of 7.5 or more and 12 or less:

(A): one or more azo dyes selected from the group consisting of the following (A-1), (A-2) and (A-3):

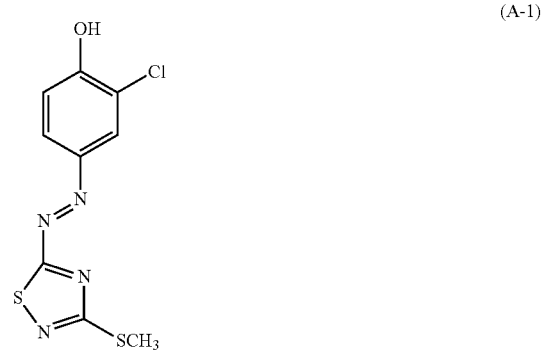

(A-1)

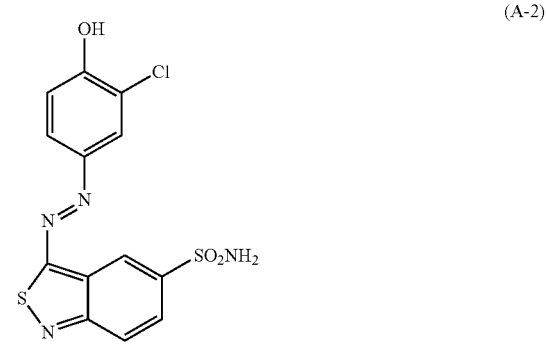

(A-2)

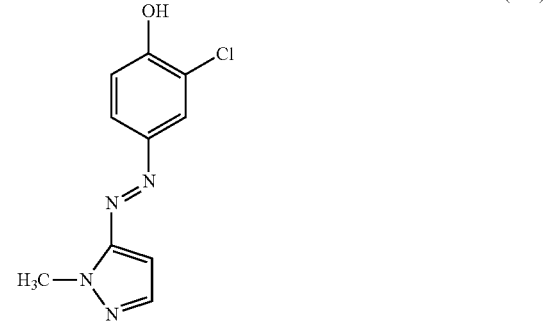

(A-3)

(Continued)

(B): a cationic compound
(C): 0.1 mass % or more and 8 mass % or less of at least one alkali metal salt of an acid selected from the group consisting of hydrochloric acid, carbonic acid and sulfuric acid.

13 Claims, No Drawings

(56) References Cited

U.S. PATENT DOCUMENTS

| | | | |
|---|---|---|---|
| 2004/0019982 A1* | 2/2004 | Pratt | A61K 8/466 8/405 |
| 2010/0229314 A1 | 9/2010 | Takiguchi | |
| 2012/0207689 A1* | 8/2012 | Konno | A61K 8/046 424/62 |

FOREIGN PATENT DOCUMENTS

| | | | |
|---|---|---|---|
| EP | 3 153 154 | 4/1917 | |
| EP | 2 606 875 | 6/2013 | |
| EP | 2 883 530 | 6/2015 | |
| EP | 2 883 531 A1 | 6/2015 | |
| JP | 3-170413 A | 7/1991 | |
| JP | 2003-342139 A | 12/2003 | |
| JP | 2010-6804 A | 1/2010 | |
| JP | 2010-24158 A | 2/2010 | |
| WO | WO 2013/092903 | 6/2013 | |
| WO | WO 2013/092903 A1 * | 6/2013 | A61Q 5/10 |
| WO | WO 2013/092904 A2 | 6/2013 | |

OTHER PUBLICATIONS

International Search Report dated Aug. 11, 2015 in PCT/JP2015/066279 filed Jun. 5, 2015.
Combined Office Action and Written Opinion dated Aug. 16, 2017 in Singaporean Patent Application No. 11201610204T.
Extended European Search Report in corresponding European Patent Application No. 15802537.9, dated Dec. 11, 2017.
Rixt T. Buwalda, et al., "Aggregation of Azo Dyes with Cationic Amphiphiles at Low Concentrations in Aqueous Solution", Langmuir, 1999, 15 (4), pp. 1083-1089.

* cited by examiner

HAIR DYE COMPOSITION

CROSS REFERENCE TO RELATED APPLICATION

This application is a 371 of PCT/JP2015/066279, filed on Jun. 5, 2015, and claims priority to the following Japanese Patent Applications: i) 2104-117908, filed on Jun. 6, 2014; ii) 2014-117909, filed on Jun. 6, 2014; and iii) 2014-117910, filed on Jun. 6, 2014.

FIELD OF THE INVENTION

The present invention relates to a hair dye composition and a method for dyeing hair using the composition.

BACKGROUND OF THE INVENTION

Hair dyes are classified depending upon the types of dyestuff used or whether or not the hair dyes have a melanin bleaching action. Typical examples of hair dyes include two-agent type permanent hair dyes consisting of a first agent containing an alkali agent, an oxidation dye and an optional direct dye such as a nitro dye and a second agent containing an oxidizing agent; and one-agent type semipermanent hair dyes containing an organic acid or an alkali agent and a direct dye such as an acid dye, a basic dye and a nitro dye.

Patent Document 1 proposes an azo dye containing a dissociative proton as a direct dye suitable for use in dyeing the hair and teaches that hair-dyeability is produced in an anionic state where a dissociative proton(s) dissociates in an alkaline condition.

(Patent Document 1) JP-A-2003-342139

SUMMARY OF THE INVENTION

The present invention provides a hair dye composition comprising the following components (A), (B) and (C) and having pH (25° C.) of 7.5 or more and 12 or less:

(A): one or more azo dyes selected from the group consisting of the following (A-1), (A-2) and (A-3):

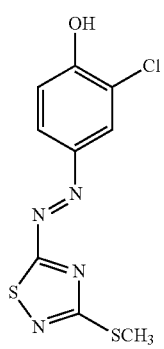

(A-1)

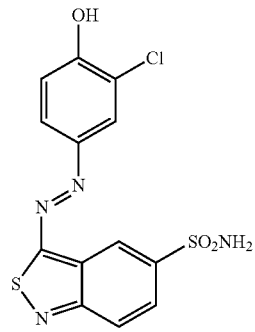

(A-2)

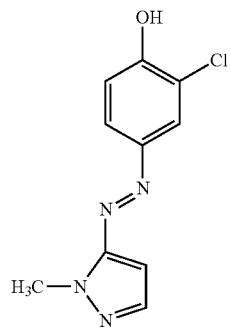

(A-3)

(B): a cationic compound (C): 0.1 mass % or more and 8 mass % or less of at least one alkali metal salt of an acid selected from the group consisting of hydrochloric acid, carbonic acid and sulfuric acid.

The present invention further provides use of the hair dye composition for dyeing hair.

The present invention further provides a method for dyeing hair by applying the hair dye composition to the hair, allowing the composition to stand for 1 to 60 minutes and washing away the composition.

DETAILED DESCRIPTION OF THE INVENTION

When the hair is placed in an alkaline condition, the hair itself is swollen and proteins and lipids elute out from the inside. As a result, the hair is damaged and the feel of the hair after application of a hair dye significantly deteriorates. In the meantime, it is known that a cationic polymer, if it is contained in a hair dye composition, suppresses dripping during hair dyeing and simultaneously gives a satisfactory texture to the hair. It is also known that a cationic surfactant, if it is contained in a hair dye composition, improves a feel of the hair after application of a hair dye.

However, if such a cationic compound is blended with a hair dye composition containing an anion-state azo dye as mentioned above, a salt is formed between the azo dye and the cationic compound. Since precipitates are formed in the hair dye composition for this reason, not only handling in blending and appearance deteriorate but also a satisfactory feel upon application cannot be provided. In addition to these problems, the composition is easily washed out during rinsing and hair-dyeability deteriorates.

Then, hair-dyeability deteriorated is conceivably recovered by increasing the used amount of dye. However, the increase of dye in amount sometimes generates a harmful effect on the stability of the formulation. Because of this, there is a limitation to increase the amount of dye.

Accordingly, the present invention relates to a hair dye composition stably containing a cationic compound and a dissociative azo dye without forming a salt, being excellent in operability in hair dyeing and satisfactory in hair-dyeability, and providing an excellent feel to the hair after hair dyeing.

The present inventors found that if a dissociative azo dye having a predetermined structure and a cationic compound are used in combination in the presence of an alkali metal salt, the dissociative azo dye and the cationic compound are stably contained without forming a salt even in an alkaline condition and that an effect of dyeing the hair brilliantly and an effect of providing an excellent feel to the hair after hair dyeing (provides an excellent feel particularly during rinsing) are provided.

<Component (A): Azo Dyes>

The hair dye composition of the present invention contains one or more azo dyes selected from the group consisting of the following (A-1), (A-2) and (A-3), as a component (A).

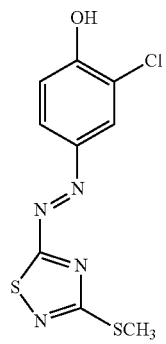
(A-1)

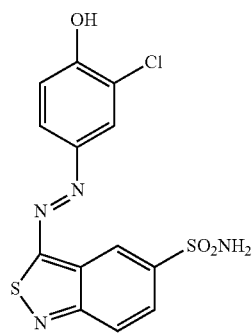
(A-2)

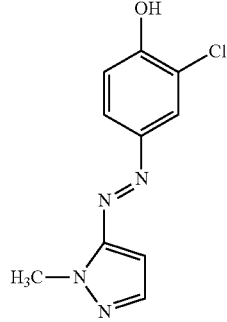
(A-3)

Note that, the pKa values of the azo dyes (A-1), (A-2) and (A-3) are 6.0, 6.0 and 7.5, respectively. Thus, in the hair dye composition of the present invention having pH (25° C.) of 7.5 to 12, almost 80% or more of these azo dyes are present in an anionic state where a proton(s) is dissociated. When a proton(s) dissociates, (A-1) displays red, (A-2) blue and (A-3) yellow.

The total content of the azo dyes in a whole composition is, in view of the stability of formulation, preferably 0.005 mass % or more, more preferably 0.01 mass % or more, further preferably 0.05 mass % or more and further preferably 0.1 mass % or more; and preferably 5 mass % or less, more preferably 3 mass % or less, further preferably 2.5 mass % or less, further preferably 1.5 mass % or less and further preferably 1 mass % or less. Note that the hair dye composition of the present invention can use a dye other than the azo dyes (A-1), (A-2) and (A-3), in combination. However, in order not to affect dyeability of a component (A), it is preferable that the total content of the azo dyes (A-1), (A-2) and (A-3) is 1 mass % or more and 100 mass % or less of in all the dyes, further 5 mass % or more and 100 mass % or less, further 10 mass % or more and 100 mass % or less and further 20 mass % or more and 100 mass % or less.

<Oxidation Dye>

In the case where the hair dye composition of the present invention is a two-agent type or three-agent type compositions, not only the azo dyes but also an oxidation dye can be added in the first agent. As a preferable oxidation dye for the hair dye composition of the present invention, a precursor and a coupler known in the art and used in conventional hair dyes can be used.

Examples of the precursor include para-phenylenediamine, toluene-2,5-diamine, 2-chloroparaphenylenediamine, para-aminophenol, para-methylaminophenol, ortho-aminophenol, 2,4-diaminophenol, N-phenyl-paraphenylenediamine and salts of these.

Examples of the coupler include meta-phenylenediamine, 2,4-diaminophenoxyethanol, meta-aminophenol, 2-methyl-5-aminophenol, 2-methyl-5-(2-hydroxyethylamino)phenol, resorcin, 1-naphthol, 1,5-dihydroxynaphthalene, hydroquinone and salts of these.

The precursors and couplers are individually used singly or in combination of two or more. The total content thereof in a whole composition is preferably set as long as the dyeability of the azo dyes is not affected. The total content is preferably 0.01 mass % or more and more preferably 0.1 mass % or more; and preferably 5 mass % or less, more preferably 3 mass % or less, further preferably 2 mass % or less, further preferably 1 mass % or less and further preferably 0.5 mass % or less.

<Direct Dye Other than Component (A)>

In the hair dye composition of the present invention, a direct dye other than the azo dyes (A-1), (A-2) and (A-3) can be further contained. In the case where the hair dye composition of the present invention is a two-agent type hair dye, a direct dye other than the azo dyes (A-1), (A-2) and (A-3) can be further contained in the first agent. As the direct dye, an acid dye, a basic dye and a dispersive dye known in the art and available in hair dyes can be used.

Examples of the acid dye include Blue No. 1, Purple No. 401, Black No. 401, Orange No. 205, Red No. 227, Red No. 106, Yellow No. 203 and Acidic Orange 3. Examples of the basic dye include Basic Blue 99, Basic Blown 16, Basic Blown 17, Basic Red 76 and Basic yellow 57.

Examples of the direct dye other than the acid dyes and basic dyes include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, N,N-bis(2-hydroxyethyl)-2-nitro-p-phenylenediamine, dispersive Purple 1, dispersive Blue 1, dispersive Black 9, HC Blue 2, HC Orange 1, HC Red 1, HC Red 3, HC Yellow 2, HC Yellow 4 and HC Yellow 5.

These direct dyes other than the azo dyes (A-1), (A-2) and (A-3) can be used singly or in combination of two or more. The content thereof in a whole composition is preferably 0.001 mass % or more and more preferably 0.01 mass % or more; and preferably 5 mass % or less, more preferably 3 mass % or less, further preferably 2 mass % or less, further preferably 1 mass % or less and further preferably 0.5 mass % or less.

<Component (B): Cationic Compound>

As the cationic compound as the component (B), a cationic polymer (B1) and a cationic surfactant (B2) are included.

<Component (B1): Cationic Polymer>

The hair dye composition of the present invention contains a cationic polymer. The cationic polymer herein refers to a water-soluble polymer having a cationic group or a group which can be ionized to be a cationic group. An ampholytic polymer wholly acting as a cation is also included.

The nitrogen content of a cationic polymer of component (B1) is, in order to suppress dripping and improve the feel (of hair) during rinsing a composition, preferably 0.3 mass % or more, more preferably 0.8 mass % or more, further preferably 1.4 mass % or more, further preferably 2.4 mass % or more, further preferably 3.0 mass % or more, further preferably 4.0 mass % or more and further preferably 5.0 mass % or more; and preferably 9.0 mass % or less and more preferably 8.8 mass % or less.

The nitrogen content of the component (B1) is measured by neutralization titration as follows. An arbitrary amount (0.5 to 10 g) of the component (B1) is sampled and dissolved in about 10 times the amount of a solution mixture of isopropyl alcohol and toluene (1:1 [volume ratio]). Tetrabromophenolphthalein ethyl ester potassium is added as an indicator. The resultant solution is subjected to neutralization titration with an aqueous perchloric acid solution. The content is calculated in terms of a nitrogen atom in 1 g of the component (B1) based on the amount of the sample taken above, normality and consumed amount of the aqueous perchloric acid solution.

As the cationic polymer to be used in the present invention, cationic derivatives represented by a cationic cellulose derivative, cationic guar gum, a quaternized polyvinylpyrrolidone derivative, a diallyl quaternized ammonium salt polymer derivative are included. Examples thereof include a hydroxyethylcellulose/dimethyl diallyl ammonium chloride copolymer, hydroxyethylcellulose-hydroxypropyl trimethyl ammonium chloride, a cationized vinylpyrrolidone/dimethylaminoethyl methacrylate copolymer, a dimethyl diallyl ammonium chloride homopolymer, a dimethyl diallyl ammonium chloride/acrylamide copolymer, a dimethyl diallyl ammonium chloride/acrylic acid copolymer and a dimethyl diallyl ammonium chloride/acrylic acid/acrylamide copolymer.

Specific examples thereof include a dimethyl diallyl ammonium chloride polymer (polyquaternium-6; for example, Merquat 100 (nitrogen content: 8.7 mass %, Japan LUBRIZOL)); a dimethyl diallyl ammonium chloride/acrylic acid copolymer (polyquaternium-22; for example, Merquat 280 (nitrogen content: 7.0 mass %, Japan LUBRIZOL) and Merquat 295 (nitrogen content: 8.3 mass %, Japan LUBRIZOL)); a dimethyl diallyl ammonium chloride/acrylamide copolymer (polyquaternium-7; for example, Merquat 550 (nitrogen content: 4.5 mass %, Japan LUBRIZOL)); a dimethyl diallyl ammonium chloride/acrylic acid/acrylamide polymer (polyquaternium-39; for example, Merquat 3331 PR (nitrogen content: 3.8 mass %, Japan LUBRIZOL)); a diethyl sulfate solution of a vinylpyrrolidone/N,N-dimethylaminoethyl methacrylate copolymer (polyquaternium-11; for example, Gafcut 734 (nitrogen content: 0.3 to 0.4 mass %, ISP Japan) and Gafcut 755 N (nitrogen content: 0.4 to 0.6 mass %, ISP Japan)); and O-[2-hydroxy-3-(trimethylammonio)propyl]hydroxyethylcellulose chloride (polyquaternium-10; for example, UCARE polymer JR-400 (nitrogen content: 1.5 to 2.2 mass %, Dow Chemical), POIZ C-60H (nitrogen content: 2.0 mass %, Kao Corp.), POIZ C-150L (nitrogen content: 1.0 to 1.2 mass %, Kao Corp.) and CATICELLO M-80 (nitrogen content: 1.5 mass %, Kao Corp.)). Of these, in order to suppress dripping and improve the feel during rinsing a composition, a dimethyl diallyl ammonium chloride polymer, a dimethyl diallyl ammonium chloride/acrylic acid copolymer and a dimethyl diallyl ammonium chloride/acrylamide copolymer are preferable.

The cationic polymers (B1) may be used in combination of two or more. The content thereof in a whole composition is, in view of conditioning effect and operability in hair dyeing, preferably 0.01 mass % or more, more preferably 0.1 mass % or more, further preferably 0.5 mass % or more and further preferably 1 mass % or more; and preferably 10 mass % or less, more preferably 6 mass % or less, further preferably 5 mass % or less, further preferably 4 mass % or less and further preferably 3 mass % or less.

<Component (B2): Cationic Surfactant>

The hair dye composition of the present invention contains a cationic surfactant as a component (B2). As the cationic surfactant, the compound represented by the following formula (1) can be used.

$$R^4-\underset{\underset{R^3}{|}}{\overset{\overset{R^1}{|}}{N^+}}-R^2 \quad X^-  \quad (1)$$

In the formula, $R^1$, $R^2$, $R^3$ and $R^4$ each independently represent a hydrogen atom or a hydrocarbon group; one or two of $R^1$, $R^2$, $R^3$ and $R^4$ are a hydrocarbon group having 8 to 36 carbon atoms and the remainders represent a hydrogen atom or a hydrocarbon group having 1 to 7 carbon atoms; and $X^-$ represents an anion.

Examples of the hydrocarbon group herein include a linear or branched alkyl group, a linear or branched alkenyl group, an aryl group and an aralkyl group.

One or two (preferably one) of $R^1$, $R^2$, $R^3$ and $R^4$ are preferably a linear or branched alkyl group having 8 to 30 carbon atoms, further preferably 10 to 24 carbon atoms and further preferably 12 to 18 carbon atoms; and the remainders preferably represent a hydrogen atom or an alkyl group having 1 to 3 carbon atoms, further preferably 1 or 2 carbon atoms and further preferably a single carbon atom.

Examples of the anion include a chloride ion, a bromide ion, an iodide ion, a methyl sulfate ion, an ethyl sulfate ion, an acetate ion, a phosphate ion, a sulfate ion, a lactate ion and a saccharin ion. Of them, in view of availability, a chloride ion and a bromide ion are preferable.

As the component (B2), in order to provide excellent feel to the hair after hair dyeing, a monoalkyl trimethyl ammonium chloride, a dialkyldimethyl ammonium chloride and a monoalkyl trimethyl ammonium bromide are preferable. Of them, lauryl trimethyl ammonium chloride, cetyl trimethyl ammonium chloride, stearyl trimethyl ammonium chloride and behenyl trimethyl ammonium chloride are more preferable and a mixture of these is also preferable.

The cationic surfactants (B2) can be used in combination of two or more. The content of a cationic surfactant in a whole composition is, in order to provide excellent feel to the hair after hair dyeing, preferably 0.05 mass % or more, more preferably 0.1 mass % or more and further preferably 0.3 mass % or more; and preferably 20 mass % or less, more preferably 18 mass % or less, further preferably 15 mass % or less, further preferably 10 mass % or less, further preferably 5 mass % or less, further preferably 3 mass % or less, further preferably 1.5 mass % or less and further preferably 1 mass % or less.

The molar ratio of an azo dye of a component (A) to a cationic compound of a component (B), (A)/(B), in a whole composition is, in order to suppress dripping during hair dyeing, provide satisfactory texture to the hair and improve hair-dyeability, preferably 0.01 or more, more preferably 0.05 or more and further preferably 0.08 or more; and preferably 2 or less, more preferably 1.5 or less and further preferably 1 or less.

<Component (C): Alkali Metal Salt of Hydrochloric Acid, Carbonic Acid or Sulfuric Acid>

The hair dye composition of the present invention contains at least one alkali metal salt of an acid selected from the group consisting of hydrochloric acid, carbonic acid and sulfuric acid, as a component (C) in an amount of 0.1 mass % or more and 8 mass % or less, in view of the stability of a composition (formulation) and in order to provide an effect of dyeing the hair brilliantly and a satisfactory feel upon application.

The alkali metal salt of hydrochloric acid, carbonic acid or sulfuric acid serving as a component (C) is a compound obtained by substituting a part or whole of hydrogen atoms of hydrochloric acid, carbonic acid or sulfuric acid with an alkali metal(s). In view of feel of dried hair after a hair-dye treatment, a potassium salt and a sodium salt are preferable. Specific examples thereof include sodium chloride, potassium chloride, sodium carbonate, sodium hydrogen carbonate, potassium carbonate, potassium hydrogen carbonate, sodium sulfate and potassium sulfate.

These components (C) can be used in combination of two or more. The content thereof in a whole composition is, in order to stably contain a component (A) and a component (B) without forming a less soluble salt, 0.1 mass % or more, preferably 0.2 mass % or more, more preferably 0.3 mass % or more, further preferably 0.5 mass % or more and further preferably 0.6 mass % or more; and in order to allow substances to remain on hair after hair dyeing, mass % or less, preferably 7 mass % or less, more preferably 6 mass % or less, further preferably 5 mass % or less, further preferably 4 mass % or less, further preferably 3 mass % or less and further preferably 2 mass % or less.

The molar ratio of a whole component (B) relative to the total of a component (A) and a component (C) in a whole composition, (B)/[(A)+(C)], is, in order to improve dyeability and the stability of a composition, preferably 0.005 or more, more preferably 0.01 or more, further preferably 0.02 or more, further preferably 0.03 or more, further preferably 0.05 or more and further preferably 0.08 or more; and preferably 10 or less, more preferably 8 or less, further preferably 7 or less, further preferably 5 or less, further preferably 4 or less, further preferably 3 or less, further preferably 2 or less, further preferably 1.5 or less and further preferably 1 or less.

The mass ratio of a component (B1) relative to the total of a component (A) and a component (C) in a whole composition, (B1)/[(A)+(C)], is, in order to improve dyeability and the stability of a composition, preferably 0.01 or more, more preferably 0.05 or more, further preferably 0.08 or more, further preferably 0.14 or more and further preferably 0.2 or more; and preferably 6 or less, more preferably 4 or less, further preferably 3 or less, further preferably 2 or less, further preferably 1 or less, further preferably 0.9 or less and further preferably 0.5 or less.

The mass ratio of a component (B2) relative to the total of a component (A) and a component (C) in a whole composition, (B2)/[(A)+(C)], is, in order to improve dyeability and the stability of a composition, preferably 0.01 or more, more preferably 0.05 or more, further preferably 0.08 or more, further preferably 0.15 or more, further preferably 0.2 or more; and preferably 6 or less, more preferably 4 or less, further preferably 3 or less, further preferably 2 or less, further preferably 1 or less and further preferably 0.9 or less.

<Component (D): Anionic Surfactant or Nonionic Surfactant>

The hair dye composition of the present invention can further contain an anionic surfactant (D1) or a nonionic surfactant (D2) as a component (D).

Examples of the anionic surfactant as the component (D1) include an alkylbenzene sulfonate salt, an alkyl or alkenyl ether sulfate salt, an alkyl or alkenyl sulfate salt, an olefin sulfonate salt, an alkane sulfonate salt, a saturated or unsaturated fatty acid salt, an alkyl or alkenyl ether carboxylate salt, an α-sulfo fatty acid salt, a N-acylamino acid, a phosphoric acid mono- or diester and a sulfosuccinic acid ester. Examples of the alkyl ether sulfate salt include polyoxyethylene alkyl ether sulfate salt. Examples of the counter ions to the anionic groups of these anionic surfactants include alkali metal ions such as a sodium ion and a potassium ion; alkaline earth metal ions such as a calcium ion and a magnesium ion; an ammonium ion; and an alkanolamine having 1 to 3 alkanol groups having 2 or 3 carbon atoms (for example, monoethanolamine, diethanolamine, triethanolamine, triisopropanolamine).

Examples of the nonionic surfactant as the component (D2) include a polyoxyalkylene alkyl ether, a polyoxyalkylene alkenyl ether, a higher fatty acid sucrose ester, a polyglycerin fatty acid ester, a higher fatty acid mono- or di-ethanolamide, polyoxyethylene hardened castor oil, a polyoxyethylene sorbitan fatty acid ester, a polyoxyethylene sorbitol fatty acid ester, an alkyl saccharide, an alkylamine oxide and an alkylamidoamine oxide. Of them, a polyoxyalkylene alkyl ether, a polyoxyethylene hardened castor oil and an alkyl saccharide are preferable, a polyoxyethylene alkyl (12 to 14) ether and an alkyl polyglucoside are more preferable.

Of these anionic surfactants (D1) and nonionic surfactants (D2), an alkyl sulfate salt, a polyoxyalkylene alkyl sulfate salt, a fatty acid salt, an alkyl ether carboxylate salt, an alkyl glyceryl ether and an alkyl polyglucoside are preferable.

The components (D) can be used in combination of two or more. The content of the component (D) in a whole composition is, in view of foamability of the formulation, preferably 0.1 mass % or more and more preferably 0.5 mass % or more; and preferably 20 mass % or less, more preferably 10 mass % or less and further preferably 5 mass % or less.

The mass ratio of a component (B2) relative to the total of a component (A) and a component (D1), (B2)/[(A)+(D1)], is, in order to blend them stably in a composition and provide an excellent feel to the hair after hair dyeing, preferably 1.2 or less, more preferably 1 or less, further preferably 0.95 or less, further preferably 0.85 or less and further preferably 0.75 or less; and preferably 0.01 or more, more preferably 0.05 or more, further preferably 0.1 or more, further preferably 0.15 or more, further preferably 0.20 or more, further preferably 0.25 or more and further preferably 0.35 or more.

<Surfactant Other than Component (D)>

The hair dye composition of the present invention can contain a surfactant other than the component (D). As other surfactants, either a cationic surfactant or an amphoteric surfactant can be used.

As the cationic surfactant, in order to provide an excellent feel to the hair after hair dyeing, a monoalkyl trimethyl ammonium chloride, a dialkyl dimethyl ammonium chloride and monoalkyl trimethyl ammonium bromide are preferable. Of them, stearyl trimethyl ammonium chloride (steartrimonium chloride), cetyl trimethyl ammonium chloride (cetrimonium chloride), lauryl trimethyl ammonium chloride (lauryl trimonium chloride) are more preferable. These are preferably used as a mixture of two or more.

Examples of the amphoteric surfactant include imidazoline, carbobetaine, amidobetaine, sulfobetaine, hydroxysulfobetaine and amidosulfobetaine. A betaine surfactant such as an alkyl dimethylaminoacetic acid betaine and a fatty acid amidopropylbetaine is more preferable and a fatty acid amidopropylbetaine is further preferable.

The surfactants other than the component (D) can be used in combination of two or more. The content thereof in a whole composition is, in view of satisfactory feel and emulsification performance, preferably 0.1 mass % or more, more preferably 0.2 mass % or more and further preferably 0.5 mass % or more; and preferably 20 mass % or less, more preferably 10 mass % or less and further preferably 5 mass % or less.

<Component (E): Alkali Agent>

To the hair dye composition of the present invention, an alkali agent can be further contained. In the case where the hair dye composition of the present invention is a two-agent type or three-agent type composition, the alkali agent is contained in a first agent. Examples of the alkali agent include ammonia and a salt thereof, sodium hydroxide, potassium hydroxide, alkanolamines such as monoethanolamine, isopropanolamine, 2-amino-2-methylpropanol and 2-aminobutanol and salts thereof; alkane diamines such as 1,3-propanediamine and a salt thereof; and carbonates such as sodium carbonate, potassium carbonate, sodium hydrogen carbonate, potassium hydrogen carbonate and guanidine carbonate.

The alkali agents may be used in combination of two or more. The content thereof in a whole composition is, in order to produce a sufficient hair dyeing effect, preferably 0.01 mass % or more, further 0.05 mass % or more, further 0.1 mass % or more, and further 0.2 mass % or more; and in order to reduce hair damage and scalp irritation, preferably 20 mass % or less, further 10 mass % or less, further 5 mass % or less and further 4 mass % or less.

<pH Adjuster>

In the hair dye composition of the present invention, a pH adjuster can be further contained. Examples of the pH adjuster include not only alkali agents as mentioned above but also inorganic acids such as hydrochloric acid and phosphoric acid; and organic acids such as citric acid, glycolic acid and lactic acid.

<Oxidizing Agent>

In the case where the hair dye composition of the present invention is a two-agent type or three-agent type composition, an oxidizing agent is contained in the second agent. In this case, dyeing and bleaching are simultaneously performed to obtain more brilliant color of hair. The azo dye to be used in the present invention is very stable to an oxidizing agent.

Examples of the oxidizing agent include hydrogen peroxide; persulfates such as ammonium persulfate, potassium persulfate and sodium persulfate; perborates such as sodium perborate; percarbonates such as sodium percarbonate; and bromates such as sodium bromate and potassium bromate. Of them, in view of bleaching of hair and stability and effectiveness of an oxidizing agent itself, hydrogen peroxide is preferable. Furthermore, hydrogen peroxide can be used in combination with other oxidizing agents serving as oxidizing aids. Of the oxidizing agents, a persulfate is preferably used in combination with hydrogen peroxide.

The oxidizing agents, when used, can be used singly or in combination of two or more. The content thereof in a whole composition is, in order to obtain a sufficient hair dyeing effect, preferably 0.1 mass % or more, further 0.5 mass % or more and further 1.0 mass % or more; and in order to reduce hair damage and scalp irritation, preferably 12.0 mass % or less, further 9.0 mass % or less and further 6.0 mass % or less.

When hydrogen peroxide is used in combination with a persulfate, it is preferable that the content of hydrogen peroxide in a whole composition is 0.5 mass % or more and 10 mass % or less; the content of the persulfate in a whole composition is 0.5 mass % or more and 25 mass % or less; and the total content of both compounds is 1 mass % or more and 30 mass % or less.

<Water-Soluble Polymer>

In the hair dye composition of the present invention, a water-soluble polymer can be contained in order to prevent dripping upon application and deposition of dirt on e.g., the scalp. Examples of the water-soluble polymer include gum Arabic, carrageenan, karaya gum, tragacanth gum, carob gum, quince seed (quince), casein, dextrin, gelatin, sodium pectate, sodium alginate, methylcellulose, ethylcellulose, carboxymethylcellulose (CMC), hydroxyethylcellulose, hydroxypropylcellulose, polyvinyl alcohol (PVA), polyvinyl methyl ether (PVM), polyvinylpyrrolidone (PVP), sodium polyacrylate, locust bean gum, guar gum, tamarind gum, dialkyl dimethyl ammonium cellulose sulfate, xanthan gum, modified xanthan gum, welan gum, Rhaball gum, gellan gum, a carboxyvinyl polymer, an acrylate/methacrylate copolymer, a methyl vinyl ether-maleic anhydride copolymer partially crosslinked with 1,9-decadiene, polyethylene glycol, magnesium aluminum silicate and bentonite. Of them, hydroxyethylcellulose, xanthan gum and modified xanthan gum are preferable.

These water-soluble polymers can be used singly or in combination of two or more. The content thereof in a whole composition is preferably 0.1 mass % or more and more preferably 0.5 mass % or more; and preferably 10 mass % or less and more preferably 5 mass % or less.

<Conditioning Component>

The hair dye composition of the present invention can contain a conditioning component suitable for applying to the hair other than a cationic polymer serving as the component (B). The conditioning component is a polymer or oil soluble or dispersible in a hair dye composition and deposits onto the hair when a hair dye composition is washed away or diluted with water and shampoo.

Example of the conditioning component suitable for use in the hair dye composition of the present invention include silicones (for example, silicone oil, cationic silicone, silicone gum, silicone resin), organic conditioning oils (for example, a hydrocarbon oil, a polyolefin, a fatty acid ester), aliphatic amides and polyalkylene glycols.

These conditioning components can be used singly or in combination of two or more. The content thereof in a whole composition is preferably 0.01 mass % or more, more preferably 0.05 mass % or more and further preferably 0.5 mass % or more; and preferably 20 mass % or less, more preferably 15 mass % or less and further preferably 5 mass % or less.

<Organic Solvent>

The hair dye composition of the present invention may contain an organic solvent. Examples of the organic solvent include lower alkanols such as ethanol, 1-propanol and 2-propanol; aromatic alcohols such as benzyl alcohol, 2-benzyloxy ethanol and phenoxyethanol; polyols such as propylene glycol, 1,3-butanediol, diethylene glycol and glycerin; ether alcohols such as ethoxy ethanol, ethoxy diglycol and methoxy ethanol; N-alkyl pyrrolidones such as N-methylpyrrolidone and N-ethyl pyrrolidone; alkylene carbonates such as propylene carbonate; and lactones such as γ-valerolactone and γ-caprolactone.

These organic solvents can be used singly or in combination of two or more. The content thereof in a whole composition is preferably 0.1 mass % or more, more preferably 1 mass % or more and further preferably 2 mass % or more; and preferably 35 mass % or less, more preferably 30 mass % or less and further preferably 25 mass %.

<Medium>

In the hair dye composition of the present invention, water is used as a medium. It is preferable that the content of water in a hair dye composition is 10 mass % or more, further 20 mass % or more, further 30 mass % or more and further 40 mass % or more and further 50 mass % or more; and 95 mass % or less, further 90 mass % or less and further 85 mass % or less.

<Other Optional Components>

In the hair dye composition of the present invention, other components used as normal cosmetic raw materials can be added other than the aforementioned components.

Such optional components can be added for the blending purpose of viscosity modification, pearling, preservation, sequestering, stabilization, anti-oxidation, ultraviolet absorption, moisturization, product coloring and perfuming. Examples of the specific optional components include animal and vegetable fats and oils, higher fatty acids, protein hydrolysates, protein derivatives, amino acids, plant extracts, vitamins, dyes and fragrances.

<Dosage Form>

The hair dye composition of the present invention can be used as one-agent type, two-agent type, or three-agent type hair dye. The one-agent type hair dye composition consists of a single agent containing a component (A). The two-agent type hair dye composition preferably consists of a first agent containing a component (A) and an alkali agent and a second agent containing hydrogen peroxide. The three-agent type hair dye composition preferably consists of a first agent containing an oxidation dye and/or direct dye other than a component (A) and an alkali agent, a second agent containing hydrogen peroxide and a third agent containing the component (A); or consists of a first agent containing a component (A) and an alkali agent, a second agent containing hydrogen peroxide and a third agent containing other components. As the third agent containing the other components, a powdery oxidizing agent formed of granules of a persulfate (e.g., ammonium persulfate, potassium persulfate, sodium persulfate) is preferably used for improving bleaching power.

Note that, in the present invention, "the whole composition" refers the entire composition to be applied to the hair-dye treatment. In the case of the two-agent type hair dye, a mixture prepared by mixing a first agent and a second agent is referred to and in the three-agent type hair dye, a mixture of a first agent, a second agent and a third agent is referred to.

The hair dye composition of the present invention can be used, for example, in the form of liquid, emulsion, cream, gel, paste and mousse and prepared in the form of aerosol. In these cases, it is desirable to control the viscosity of the whole composition so as to rarely drip out when the composition is applied to the hair. The viscosity of the whole composition (25° C.) is preferably 2,000 to 200,000 mPa·s, more preferably 4,000 to 150,000 mPa·s, further preferably 6,000 to 100,000 mPa·s and further preferably 8,000 to 80,000 mPa·s, as a measurement value obtained by a type-B rotational viscometer with a helical stand (model; digital viscometer TVB-10, Toki Sangyo Co., Ltd.) after the composition is rotated by use of rotor T-C at 10 rpm for one minute. Note that, in the case of a two-agent type or three-agent type composition, it is specified that the viscosity of the composition is determined 3 minutes after blending individual agent.

The hair dye composition of the present invention is foamed by ejecting from a non-aerosol foamer or shaking in a cup and then applied to the hair. In this case, it is desirable to control the viscosity of the whole composition before foamed so as to avoid dripping when the composition is foamed and applied to the hair. The viscosity of the whole composition (25° C.) is preferably 1 to 800 mPa·s, more preferably 1 to 600 mPa·s, further preferably 1 to 500 mPa·s, and further preferably 1 to 300 mPa·s as a measurement value measured by a type-B rotating viscometer (model; digital viscometer TV-10, Toki Sangyo Co., Ltd.) after the composition is rotated by use of rotor No. 1 at 60 rpm for one minute (note that when the viscosity excesses 160 mPa·s, a measurement value obtained after the composition is rotated at 12 rpm for one minute). Note that, in the case of a two-agent type or three-agent type composition, the viscosity of the composition is determined 3 minutes after blending individual agent.

<pH>

The pH (25° C.) of the hair dye composition of the present invention upon application (at the time of blending in the case of two-agent type or three-agent type composition) is 7.5 or more, preferably 8 or more, more preferably 8.5 or more and further preferably 9 or more; and 12 or less, preferably 11.5 or less and more preferably 11 or less, in order to obtain satisfactory hair dyeing effect and suppress skin irritation. In the case where the hair dye composition of the present invention is a two-agent type hair dye, the pH (25° C.) of the first agent is 8 or more and 12 or less, whereas pH (25° C.) of the second agent is preferably 2 or more and 5 or less. Note that, in the specification, the pH of a hair dye composition is a value measured at room temperature (25° C.) by use of a pH meter F-22 and a pH electrode 6367-10D, manufactured by Horiba, Ltd.

<Method for Producing Hair Dye Composition>

In the case where the hair dye composition of the present invention is a one-agent type composition, it is preferable that the hair dye composition is prepared by mixing a component (B) and a component (C) followed by mixing the resultant mixture and a component (A) or mixing a component (A) and a component (C) followed by mixing the resultant mixture and a component (B), in view of the stability of a hair dye composition. In the case the hair dye composition of the present invention is a two-agent type or three-agent type composition and components (A) to (C) are all contained in a first agent, it is preferable that the first agent is prepared by mixing a component (B) and a component (C), followed by mixing the resultant mixture and a component (A) or mixing a component (A) and a component (C), followed by mixing the resultant mixture and a component (B), in view of the stability of the hair dye composition.

<Method for Dyeing Hair>

Hair-dye treatment using the hair dye composition of the present invention may be performed by applying, for example, the hair dye composition of the present invention (after a first agent and a second agent are blended in the case of a two-agent type composition or after a first agent, a second agent and a third agent are mixed in the case of a three-agent type composition, right before use), allowing to stand in a predetermined time, washing away the composition, and drying the hair. The hair dye composition of the present invention is applied in 0.1 fold to 10 fold mass of the hair at an application temperature of 15 to 45° C. preferably for 1 to 60 minutes, further preferably 3 to 45 minutes and further preferably 5 to 30 minutes.

With respect to the aforementioned embodiment, preferable embodiments of the present invention will be further disclosed below.

<1> A hair dye composition comprising the following components (A), (B) and (C) and applied at pH (25° C.) of 7.5 or more and 12 or less:

(A): one or more azo dyes selected from the group consisting of the following (A-1), (A-2) and (A-3):

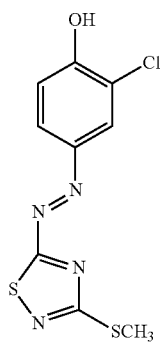

(A-1)

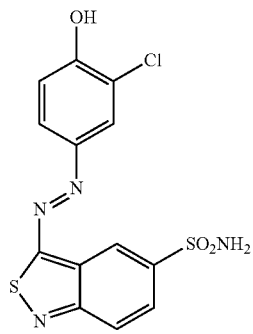

(A-2)

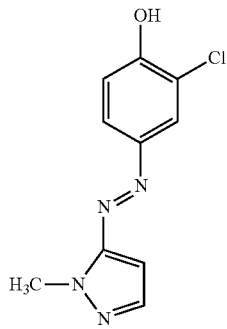

(A-3)

(B): a cationic compound (C): 0.1 mass % or more and 8 mass % or less of at least one alkali metal salt of an acid selected from the group consisting of hydrochloric acid, carbonic acid and sulfuric acid.

<2> The hair dye composition according to <1>, in which the total content of the component (A) in the whole composition is preferably 0.005 mass % or more, more preferably 0.01 mass % or more, further preferably 0.05 mass % or more and further preferably 0.1 mass % or more and; and preferably 5 mass % or less, more preferably 3 mass % or less, further preferably 2.5 mass % or less, further preferably 1.5 mass % or less and further preferably 1 mass % or less.

<3> The hair dye composition according to <1> or <2>, in which the component (B) is preferably at least one selected from the group consisting of a cationic polymer (B1) and a cationic surfactant (B2).

<4> The hair dye composition according to <3>, in which the component (B1) is preferably one or more member selected from the group consisting of a dimethyl diallyl ammonium chloride polymer, a dimethyl diallyl ammonium chloride/acrylic acid copolymer, a dimethyl diallyl ammonium chloride/acrylamide copolymer, a dimethyl diallyl ammonium chloride/acrylic acid/acrylamide copolymer, a diethyl sulfate solution of vinylpyrrolidone/N,N-dimethylaminoethyl methacrylate copolymer, O-[2-hydroxy-3-(trimethylammonio)propyl]hydroxyethylcellulose chloride and a hydroxyethylcellulose/dimethyl diallyl ammonium chloride copolymer.

<5> The hair dye composition according to <3> or <4>, in which the nitrogen content of the component (B1) is preferably 0.3 mass % or more, more preferably 0.8 mass % or more, further preferably 1.4 mass % or more, further preferably 2.4 mass % or more, further preferably 3.0 mass % or more, further preferably 4.0 mass % or more and further preferably 5.0 mass % or more; and preferably 9.0 mass % or less and more preferably 8.8 mass % or less.

<6> The hair dye composition according to any one of <3> to <5>, in which the content of the component (B1) in the whole composition is preferably 0.01 mass % or more, more preferably 0.1 mass % or more, further preferably 0.5 mass % or more and further preferably 1 mass % or more; and preferably 10 mass % or less, more preferably 6 mass % or less, further preferably 5 mass % or less, further preferably 4 mass % or less and further preferably 3 mass % or less.

<7> The hair dye composition according to any one of <3> to <6>, in which the component (B2) is preferably a cationic surfactant represented by the following formula (1):

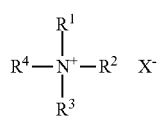

wherein, $R^1$, $R^2$, $R^3$ and $R^4$ each independently represent a hydrogen atom or a hydrocarbon group; one or two of $R^1$, $R^2$, $R^3$ and $R^4$ are a hydrocarbon group having 8 to 36 carbon atoms and the remainders represent a hydrogen atom or a hydrocarbon group having 1 to 7 carbon atoms; and $X^-$ represents an anion.

<8> The hair dye composition according to <7>, in which the component (B2) is one or more member selected from the group consisting of lauryl trimethyl ammonium chloride, cetyl trimethyl ammonium chloride, stearyl trimethyl ammonium chloride and behenyl trimethyl ammonium chloride.

<9> The hair dye composition according to any one of <3> to <8>, in which the content of the component (B2) in the whole composition is preferably 0.05 mass % or more, more preferably 0.1 mass % or more and further preferably 0.3 mass % or more; and preferably 20 mass % or less, more preferably 18 mass % or less, further preferably 15 mass % or less, further preferably 10 mass % or less, further preferably 5 mass % or less, further preferably 3 mass % or less, further preferably 1.5 mass % or less and further preferably 1 mass % or less.

<10> The hair dye composition according to any one of <1> to <9>, in which the molar ratio of the component (A) to the component (B), (A)/(B), in the whole composition is preferably 0.01 or more, more preferably 0.05 or more and further preferably 0.08 or more; and preferably 2 or less, more preferably 1.5 or less and further preferably 1 or less.

<11> The hair dye composition according to any one of <1> to <10>, in which the component (C) is one or more member preferably selected from the group consisting of sodium chloride, potassium chloride, sodium carbonate, sodium hydrogen carbonate, potassium carbonate, potassium hydrogen carbonate, sodium sulfate and potassium sulfate.

<12> The hair dye composition according to any one of <1> to <11>, in which the content of the component (C) in the whole composition is preferably 0.2 mass % or more, more preferably 0.3 mass % or more, and further preferably 0.6 mass % or more; and preferably 7 mass % or less, more preferably 6 mass % or less, further preferably 5 mass % or less, further preferably 4 mass % or less, further preferably 3 mass % or less and further preferably 2 mass % or less.

<13> The hair dye composition according to any one of <1> to <12>, in which the molar ratio of a whole component (B) relative to the total of a component (A) and a component (C) in the whole composition, (B)/[(A)+(C)], is preferably 0.005 or more, more preferably 0.01 or more, further preferably 0.02 or more, further preferably 0.03 or more, further preferably 0.05 or more and further preferably 0.08 or more; and preferably 10 or less, more preferably 8 or less, further preferably 7 or less, further preferably 5 or less, further preferably 4 or less, further preferably 3 or less, further preferably 2 or less, further preferably 1.5 or less and further preferably 1 or less.

<14> The hair dye composition according to any one of <3> to <13>, in which the mass ratio of the component (B1) relative to the total of the component (A) and the component (C) in the whole composition, (B1)/[(A)+(C)], is preferably 0.01 or more, more preferably 0.05 or more, further preferably 0.08 or more, further preferably 0.14 or more and further preferably 0.2 or more; and preferably 6 or less, more preferably 4 or less, further preferably 3 or less, further preferably 2 or less, further preferably 1 or less, further preferably 0.9 or less and further preferably 0.5 or less.

<15> The hair dye composition according to any one of <3> to <14>, in which the mass ratio of the component (B2) relative to the total of the component (A) and the component (C) in the whole composition, (B2)/[(A)+(C)], is preferably 0.01 or more, more preferably 0.05 or more, further preferably 0.08 or more, further preferably 0.15 or more and further preferably 0.2 or more; and preferably 6 or less, more preferably 4 or less, further preferably 3 or less, further preferably 2 or less and further preferably 1 or less, further preferably 0.9 or less.

<16> The hair dye composition according to any one of <1> to <15>, preferably further comprising an anionic surfactant (D1) or a nonionic surfactant (D2), as the component (D).

<17> The hair dye composition according to <16>, in which the component (D1) is one or more member selected from the group consisting of an alkylbenzene sulfonate salt, an alkyl or alkenyl ether sulfate salt, an alkyl or alkenyl sulfate salt, an olefin sulfonate salt, an alkane sulfonate salt, a saturated or unsaturated fatty acid salt, an alkyl or alkenyl ether carboxylate salt, an α-sulfo fatty acid salt, a N-acylamino acid, a phosphoric acid mono- or diester and a sulfosuccinic acid ester.

<18> The hair dye composition according to <16> or <17>, in which the mass ratio of the component (B2) relative to the total of the component (A) and the component (D1), (B2)/[(A)+(D1)], is preferably 1.2 or less, more preferably 1 or less, further preferably 0.95 or less, further preferably 0.85 or less and further preferably 0.75 or less; and preferably 0.01 or more, more preferably 0.05 or more, further preferably 0.1 or more, further preferably 0.15 or more, further preferably 0.20 or more, further preferably 0.25 or more and further preferably 0.35 or more.

<19> The hair dye composition according to <16>, in which the component (D2) is one or more member selected from the group consisting of a polyoxyalkylene alkyl ether, a polyoxyalkylene alkenyl ether, a higher fatty acid sucrose ester, a polyglycerin fatty acid ester, a higher fatty acid mono- or di-ethanolamide, polyoxyethylene hardened castor oil, a polyoxyethylene sorbitan fatty acid ester, a polyoxyethylene sorbitol fatty acid ester, an alkyl saccharide, an alkylamine oxide and an alkyl amidoamine oxide.

<20> The hair dye composition according to <16>, in which the component (D) is one or more member selected from the group consisting of an alkyl sulfate salt, a polyoxyalkylene alkyl sulfate salt, a fatty acid salt, an alkyl ether carboxylate salt, an alkyl glyceryl ether and an alkyl polyglucoside.

<21> The hair dye composition according to any one of <16> to <20>, in which the content of the component (D) in the whole composition is preferably 0.1 mass % or more, more preferably 0.2 mass % or more and further preferably 0.5 mass % or more; and preferably 20 mass % or less, more preferably 10 mass % or less and further preferably 5 mass % or less.

<22> The hair dye composition according to any one of <1> to <21>, preferably further comprising an alkali agent as a component (E).

<23> The hair dye composition according to <22> in which the content of the component (E) in the whole composition is preferably 0.01 mass % or more, more preferably 0.05 mass % or more, further preferably 0.1 mass % or more and further preferably 0.2 mass % or more; and preferably 20 mass % or less, more preferably 10 mass % or less, further preferably 5 mass % or less and further preferably 4 mass % or less.

<24> The hair dye composition according to any one of <1> to <23>, which is a two-agent type or three-agent type composition preferably comprising an oxidizing agent in a second agent.

<25> The hair dye composition according to <24>, in which the content of the oxidizing agent in the whole composition is preferably 0.1 mass % or more, more preferably 0.5 mass % or more and further preferably 1.0 mass % or more; and preferably 12.0 mass % or less, more preferably 9.0 mass % or less and further preferably 6.0 mass % or less.

<26> The hair dye composition according to any one of <1> to <25>, in which the pH at 25° C. upon application is preferably 8 or more, more preferably 8.5 or more, further preferably 9 or more; and preferably 11.5 or less and more preferably 11 or less.

<27> A method for dyeing hair by applying the hair dye compositions according to any one of <1> to <26> to the hair, allowing to stand for 1 to 60 minutes and washing away the composition.

EXAMPLES

Examples 1 to 5 and Comparative Examples 1 to 2

Hair dye compositions (one-agent type hair dye) having the compositions shown in Table 1 were prepared by the following method. The obtained hair dye compositions were evaluated for dripping, a feel during rinsing a composition, dyeability and stability thereof by the following methods. The results of these are all together shown in Table 1.

<Method for Preparing Hair Dye Composition>

In water, ammonium chloride and a component (C) were blended. After confirming dissolution of them, a component (B) was added. The mixture was stirred for a predetermined time. Then, a component (D) was added to prepare Mixture 1. Separately, ammonia and a component (A-2) were dissolved in water to prepare Mixture 2. Subsequently, Mixture 2 was blended with Mixture 1 and the resultant mixture was stirred for a predetermined time to obtain a hair dye composition.

<Dripping Evaluation>

A hair dye composition (20 g) was weighed and placed in a 200-mL elliptic cylindrical plastic bottle. The bottle was closed with a cap and shaken vigorously up and down 100 times to foam the composition. Foam corresponding to 10 g of the composition was transferred to a 200 mL-beaker and allowed to stand still for 5 minutes. Thereafter, the waste solution pooled at the bottom of the beaker was taken out by a dropper and the mass of the waste solution was measured. The smaller amount of waste solution shows that the amount of dripping of a hair dye is lower.

<Feel During Rinsing Away the Composition>

Using hair of western persons, hair tress each having a size of 5 cm in width and 23 cm in length and a weight of 8 g were prepared. A hair dye composition was applied to each of the hair tress in a bath ratio (composition:hair) of 1:1, allowed to stand at 30° C. for 20 minutes and rinsed away in water of about 40° C. At the time of rinsing, finger combability was measured by a combing force measuring device. The combing force measuring device displays the force detected by a load cell when the hair tress is hanged on a hook connecting to a load cell and sandwiched by two Denman brushes (Denman brushes D-3, total length: 204 mm, number of rows: 7, manufactured by Denman) and combed. The finger combability can be quantitatively evaluated by reading out the displayed force (see, J. Soc. Cosmet. Chem., 37, 111-124 (May/June 1986)). The force values detected by the load cell when a hair tress was combed 10 times were averaged and used as a combing force measurement value. A smaller combing force (g) means that the feel during rinsing away the composition is more excellent.

<Dyeability>

A hair dye composition was applied to a hair tress formed of white hair (1 g) of Chinese persons in a bath ratio (composition:hair) of 1:1, allowed to stand at 30° C. for 20 minutes, rinsed away with water of about 40° C., washed with a commercially available shampoo and washed with water. Then, a commercially available hair conditioner was applied to the hair tress and rinsed away with water of about 40° C. The hair tress was wiped with towel and blow-dried.

The color of the obtained hair tress immediately after hair dyeing was measured by a color-difference meter (colorimeter CR-400, manufactured by Konica Minolta Sensing, Inc.) based on the CIE color system (L*, a*, b*). The difference from the color before dyeing was obtained in accordance the following expression and used as dyeability $\Delta E^*$. The larger $\Delta E^*$ means that the dyeability is more excellent.

$$\Delta E^* = \sqrt{(L^*_1 - L^*_0)^2 + (a^*_1 - a^*_0)^2 + (b^*_1 - b^*_0)^2}$$

In the expression, $L^*_0$, $a^*_0$ and $b^*_0$ represent L*, a* and b* values of a hair tress before dyeing, respectively, and $L^*_1$, $a^*_1$ and $b^*_1$ are L*, a* and b* values of the hair tress immediately after dyeing, respectively.

<The Stability of Composition>

The stability of a hair dye composition was visually evaluated immediately after a first agent and a second agent were blended in accordance with the following criteria.

3: Transparent without precipitates

2: Cloudy without precipitates

1: Precipitates were observed

TABLE 1

|  |  | Active amount (mass %) | Comparative Example | | Example | | | | |
|---|---|---|---|---|---|---|---|---|---|
|  |  |  | 1 | 2 | 1 | 2 | 3 | 4 | 5 |
| (A) |  | Azo dye (A-2) | 0.3 | 0.3 | 0.3 | 0.3 | 0.3 | 0.3 | 0.3 |
| (B1) |  | Polyquaternium 22*[1] (nitrogen content: 7.0 mass %) | — | 1.2 | 1.2 | 1.2 | 1.2 | 1.2 | 1.2 |
| (C) |  | Sodium chloride | — | — | 1 | — | — | 0.5 | 2 |
|  |  | Potassium chloride | — | — | — | 1 | — | — | — |
|  |  | Sodium sulfate | — | — | — | — | 1 | — | — |
| (D) |  | Sodium laureth sulfate | 3.78 | 3.78 | 3.78 | 3.78 | 3.78 | 3.78 | 3.78 |
|  |  | Ammonium chloride | 0.5 | 0.5 | 0.5 | 0.5 | 0.5 | 0.5 | 0.5 |
|  |  | Ammonia | 1.2 | 1.2 | 1.2 | 1.2 | 1.2 | 1.2 | 1.2 |
|  |  | Water | Balance | Balance | Balance | Balance | Balance | Balance | Balance |
|  |  | Total | 100 | 100 | 100 | 100 | 100 | 100 | 100 |
|  |  | (B1)/[(A) + (C)] mass ratio | 0 | 4 | 0.9 | 0.9 | 0.9 | 1.5 | 0.5 |
|  |  | (B)/[(A) + (C)] molar ratio | 0 | 7.38 | 0.34 | 0.42 | 0.76 | 0.64 | 0.17 |
|  |  | (A)/(B) molar ratio | — | 0.14 | 0.14 | 0.14 | 0.14 | 0.14 | 0.14 |
|  |  | pH (25° C.) | 11 | 10.9 | 10.9 | 11 | 10.9 | 10.9 | 10.9 |
| Evaluation |  | Dripping (g) | 8.9 | 5.3 | 4 | 5.2 | 4 | 4.9 | 4.7 |
|  |  | Feel (combing force; g) during rinsing of composition | 259 | 187 | 181 | 187 | 183 | 184 | 182 |
|  |  | Dyeability (ΔE) | 51.2 | 28.3 | 44.7 | 47.1 | 43.4 | 41.2 | 44.7 |
|  |  | Stability of composition | 3 | 1 | 3 | 3 | 3 | 3 | 3 |

*[1]Merquat 280, manufactured by Japan LUBRIZOL

As shown in Table 1, the hair dye compositions of Examples 1 to 5 were excellent all in dripping, a feel during rinsing of the composition, dyeability and stability of the composition. In contrast, Comparative Example 1 was inferior in dripping, and a feel during rinsing of the composition compared to Examples 1 to 5, and Comparative Example 2 was inferior in dyeability and stability of the composition compared to Examples 1 to 5.

Examples 6 to 10 and Comparative Examples 3 and 4

The first agent and the second agent of the hair dye compositions (two-agent type hair dye) having the compositions shown in Table 2 were prepared by the following method. The hair dye compositions, each prepared by mixing the first agent and the second agent shown in Table 2 in a ratio of 1:1, were evaluated for dripping, feel during rinsing a composition, dyeability and stability of a composition in the same manner as above. The evaluation results are all together shown in Table 2.

<Method for Preparing First Agent>

In water, ammonium chloride and a component (C) were blended. After confirming dissolution of them, a component (B) was added. The mixture was stirred for a predetermined time. Then, a component (D) was added to prepare Mixture 1. Separately, ammonia and a component (A) were dissolved in water to prepare Mixture 2. Subsequently, Mixture 2 was blended with Mixture 1 and the resultant mixture was stirred for a predetermined time to obtain a first agent.

<Method for Preparing Second Agent>

In water, hydrogen peroxide and etidronic acid were blended. The mixture was stirred for a predetermined time to obtain a second agent.

TABLE 2

|  |  |  | Active amount (mass %) | Comparative Example | | Example | | | | |
|---|---|---|---|---|---|---|---|---|---|---|
|  |  |  |  | 3 | 4 | 6 | 7 | 8 | 9 | 10 |
| First agent | (A) |  | Azo dye (A-2) | 0.3 | 0.3 | 0.3 | 0.3 | 0.3 | 0.3 | 0.3 |
|  | (B1) |  | Polyquaternium 22*[1] (nitrogen content: 7.0 mass %) | — | 1.2 | 1.2 | 1.2 | 1.2 | 1.2 | 1.2 |
|  | (C) |  | Sodium chloride | — | — | 1 | — | — | 0.5 | 2 |
|  |  |  | Potassium chloride | — | — | — | 1 | — | — | — |
|  |  |  | Sodium sulfate | — | — | — | — | 1 | — | — |
|  | (D) |  | Sodium laureth sulfate | 3.78 | 3.78 | 3.78 | 3.78 | 3.78 | 3.78 | 3.78 |
|  |  |  | Ammonium chloride | 0.5 | 0.5 | 0.5 | 0.5 | 0.5 | 0.5 | 0.5 |
|  |  |  | Ammonia | 1.2 | 1.2 | 1.2 | 1.2 | 1.2 | 1.2 | 1.2 |
|  |  |  | Water | Balance | Balance | Balance | Balance | Balance | Balance | Balance |
|  |  |  | Total | 100 | 100 | 100 | 100 | 100 | 100 | 100 |
| Second agent |  |  | Hydrogen peroxide | 5.7 | 5.7 | 5.7 | 5.7 | 5.7 | 5.7 | 5.7 |
|  |  |  | Etidronic acid | 0.07 | 0.07 | 0.07 | 0.07 | 0.07 | 0.07 | 0.07 |
|  |  |  | Water | Balance | Balance | Balance | Balance | Balance | Balance | Balance |
|  |  |  | Total | 100 | 100 | 100 | 100 | 100 | 100 | 100 |
|  |  |  | (B1)/[(A) + (C)] mass ratio | 0 | 4 | 0.9 | 0.9 | 0.9 | 1.5 | 0.5 |
|  |  |  | (B)/[(A) + (C)] molar ratio | 0 | 7.38 | 0.34 | 0.42 | 0.76 | 0.64 | 0.17 |
|  |  |  | (A)/(B) molar ratio | — | 0.14 | 0.14 | 0.14 | 0.14 | 0.14 | 0.14 |
|  |  |  | pH (25° C.) | 10.4 | 10.4 | 10.4 | 10.4 | 10.4 | 10.4 | 10.4 |

TABLE 2-continued

|  |  | Comparative Example | | Example | | | | |
| --- | --- | --- | --- | --- | --- | --- | --- | --- |
|  | Active amount (mass %) | 3 | 4 | 6 | 7 | 8 | 9 | 10 |
| Evaluation | Dripping (g) | 7.9 | 5.8 | 5.8 | 5.6 | 6 | 6 | 5.5 |
|  | Feel (combing force; g) during rinsing of composition | 287.8 | 226.4 | 224.5 | 228.5 | 218.1 | 219.4 | 224.4 |
|  | Dyeability (ΔE) | 49.6 | 35.7 | 44.1 | 44.2 | 43.8 | 43 | 45.2 |
|  | Stability of composition | 3 | 1 | 3 | 3 | 3 | 3 | 3 |

*¹Merquat 280, manufactured by Japan LUBRIZOL

As shown in Table 2, the hair dye compositions of Examples 6 to 10 were excellent all in dripping, a feel during rinsing of the composition, dyeability and stability of the composition. In contrast, Comparative Example 3 was inferior in dripping and a feel during rinsing of the composition compared to Examples 6 to 10, and Comparative Example 4 was inferior in dyeability and stability of the composition compared to Examples 6 to 10.

Example 11 and Comparative Example 5

Hair dye compositions (one-agent type hair dye) having the compositions shown in Table 3 were prepared by the following method. The obtained hair dye compositions were evaluated for dripping, a feel during rinsing a composition, dyeability and stability of a composition in the same manner as above. The evaluation results of these are all together shown in Table 3.

<Method for Preparing Hair Dye Composition>

In water, isostearyl glyceryl and a component (C) were blended. After confirming dissolution of them, a component (B) was added. The mixture was stirred for a predetermined time. Then, a component (D) was added to prepare Mixture 1. Separately, monoethanolamine and components (A-1) to (A-3) were dissolved in water to prepare Mixture 2. Subsequently, Mixture 2 was blended with Mixture 1 and the resultant mixture was stirred for a predetermined time to obtain a hair dye composition.

TABLE 3

|  | Active amount (mass %) | Comparative Example 5 | Example 11 |
| --- | --- | --- | --- |
| (A) | Azo dye (A-1) | 0.05 | 0.05 |
|  | Azo dye (A-2) | 0.05 | 0.05 |
|  | Azo dye (A-3) | 0.05 | 0.05 |
| (B1) | Polyquaternium 22*¹ (nitrogen content: 8.3 mass %) | 0.19 | 0.19 |
|  | Polyquaternium 7*² (nitrogen content: 4.5 mass %) | 0.23 | 0.23 |
| (C) | Sodium sulfate | — | 1 |
| (D) | Ammonium laureth sulfate | 12 | 12 |
|  | Monoethanol amine | 1 | 1 |
|  | Isostearyl glyceryl | 0.4 | 0.4 |
|  | Water | Balance | Balance |
|  | Total | 100 | 100 |
|  | (B1)/[(A) + (C)] mass ratio | 2.8 | 0.4 |
|  | (B)/[(A) + (C)] molar ratio | 3.58 | 1.87 |
|  | (A)/(B) molar ratio | 0.28 | 0.28 |
|  | pH (25° C.) | 9.4 | 9.3 |
| Evaluation | Dripping (g) | 5.2 | 5.9 |
|  | Feel (combing force; g) during rinsing of composition | 193 | 177 |
|  | Dyeability (ΔE) | 24.7 | 29.2 |
|  | Stability of composition | 1 | 2 |

*¹Merquat 295, manufactured by Japan LUBRIZOL
*²Merquat 550, manufactured by Japan LUBRIZOL As shown in Table 3, the hair dye composition of Example 11 was excellent in dripping, a feel during rinsing of the composition, and dyeability. In contrast, Comparative Example 5 was inferior in a feel during rinsing of the composition, dyeability and stability of the composition compared to Example 11.

Examples 12 to 16

Hair dye compositions (one-agent type hair dye) having the compositions shown in Table 4 were prepared by the following method. The obtained hair dye compositions were evaluated for dyeability and the presence or absence of precipitates during blending. The evaluation results are all together shown in Table 4.

<Method for Preparing Hair Dye Composition>

In water, ammonium chloride and a component (C) were blended. After confirming dissolution of them, a component (B) was added. The mixture was stirred for a predetermined time. Then, a component (D) was added to prepare Mixture 1. Separately, ammonia and a component (A) were dissolved in water to prepare Mixture 2. Subsequently, Mixture 2 was blended with Mixture 1 and the resultant mixture was stirred for a predetermined time to obtain a hair dye composition.

TABLE 4

|  |  | Example | | | | |
| --- | --- | --- | --- | --- | --- | --- |
|  | Active amount (mass %) | 12 | 13 | 14 | 15 | 16 |
| (A) | Azo dye (A-2) | 0.05 | 0.05 | 0.05 | 0.05 | 0.05 |
| (B1) | Polyquaternium 7*¹ (nitrogen content: 4.5 mass %) | 0.27 | 0.27 | 0.27 | 0.27 | 0.27 |

TABLE 4-continued

|   | Active amount (mass %) | Example 12 | Example 13 | Example 14 | Example 15 | Example 16 |
|---|---|---|---|---|---|---|
| (C) | Sodium bicarbonate | 0.5 | 1 | 2.5 | 5 | 7.5 |
|   | Ammonium chloride | 0.5 | 0.5 | 0.5 | 0.5 | 0.5 |
|   | Ammonia | 1.76 | 1.76 | 1.76 | 1.76 | 1.76 |
| (D) | Sodium laureth sulfate | 3.78 | 3.78 | 3.78 | 3.78 | 3.78 |
|   | Water | Balance | Balance | Balance | Balance | Balance |
|   | Total | 100 | 100 | 100 | 100 | 100 |
|   | (B1)/[(A) + (C)] mass ratio | 0.49 | 0.26 | 0.11 | 0.05 | 0.04 |
|   | (B)/[(A) + (C)] molar ratio | 0.14 | 0.07 | 0.03 | 0.02 | 0.01 |
|   | (A)/(B) molar ratio | 0.16 | 0.16 | 0.16 | 0.16 | 0.16 |
|   | pH (25° C.) | 10.48 | 10.46 | 10.41 | 10.39 | 10.38 |
| Evaluation | Dyeability | 13.2 | 12.8 | 12.3 | 11.1 | 10.1 |
|   | Stability of composition | 3 | 3 | 3 | 3 | 2 |

*[1]Merquat 550, manufactured by Japan LUBRIZOL

Examples 17 to 21 and Comparative Examples 6 and 7

Hair dye compositions (one-agent type hair dye) having the compositions shown in Table 5 were prepared by the following method. The obtained hair dye compositions were evaluated for stability of a composition, dyeability and a feel during rinsing of a composition by the aforementioned methods. The results of these are all together shown in Table 5.

<Method for Preparing Hair Dye Composition>

In water, a component (C) was blended. After confirming dissolution of them, a component (B) was added. The mixture was stirred for a predetermined time to prepare Mixture 1. Separately, monoethanolamine and a component (A-2) were dissolved in water to prepare Mixture 2. Subsequently, Mixture 2 was blended with Mixture 1 and the resultant mixture was stirred for a predetermined time to obtain a hair dye composition.

Examples 22 to 26 and Comparative Examples 8 and 9

Hair dye compositions (two-agent type hair dye) having the compositions shown in Table 6 were prepared by the following method. The first agent is the same as the one-agent hair dye shown in Table 5. The hair dye compositions each prepared by mixing the first agent and the second agent shown in Table 6 in a ratio of 1:1 were evaluated for dyeability and a feel during rinsing of a composition in the same manner as above. The evaluation results are all together shown in Table 6.

<Method for Preparing First Agent>

In water, a component (C) was blended. After confirming dissolution of them, a component (B) was added. The mixture was stirred for a predetermined time to prepare Mixture 1. Separately, monoethanolamine and component (A-2) were dissolved in water to prepare Mixture 2. Subsequently, Mixture 2 was blended with Mixture 1 and the resultant mixture was stirred for a predetermined time to obtain a first agent.

<Method for Preparing Second Agent>

In water, hydrogen peroxide and etidronic acid were blended. The mixture was stirred for a predetermined time to obtain a second agent.

TABLE 5

|   | Active amount (mass %) | Comparative Example 6 | Comparative Example 7 | Example 17 | Example 18 | Example 19 | Example 20 | Example 21 |
|---|---|---|---|---|---|---|---|---|
| (A) | Azo dye (A-2) | 0.5 | 0.5 | 0.5 | 0.5 | 0.5 | 0.5 | 0.5 |
| (B2) | Steartrimonium chloride | — | 0.5 | 0.5 | 0.5 | 0.5 | 0.5 | 0.5 |
| (C) | Sodium chloride | — | — | 1 | — | — | 0.5 | 2 |
|   | Potassium chloride | — | — | — | 1 | — | — | — |
|   | Sodium sulfate | — | — | — | — | 1 | — | — |
|   | Monoethanol amine | 1.5 | 1.5 | 1.5 | 1.5 | 1.5 | 1.5 | 1.5 |
|   | Water | Balance | Balance | Balance | Balance | Balance | Balance | Balance |
|   | Total | 100 | 100 | 100 | 100 | 100 | 100 | 100 |
|   | (B2)/[(A) + (C)] mass ratio | 0 | 1.0 | 0.33 | 0.33 | 0.33 | 0.50 | 0.20 |
|   | (B)/[(A) + (C)] molar ratio | 0 | 1.06 | 0.08 | 0.10 | 0.17 | 0.15 | 0.04 |
|   | (A)/(B) molar ratio | — | 0.94 | 0.94 | 0.94 | 0.94 | 0.94 | 0.94 |
|   | pH (25° C.) | 10.7 | 10.6 | 10.6 | 10.7 | 10.7 | 10.7 | 10.6 |
| Evaluation | Stability of composition | 3 | 1 | 3 | 3 | 3 | 3 | 3 |
|   | Dyeability (ΔE) | 59.1 | 56.1 | 60.1 | 60.6 | 60.8 | 60.1 | 62.9 |
|   | Feel (combing force; g) during rinsing of composition | 241 | 218 | 190 | 189 | 192 | 193 | 187 |

As shown in Table 5, the hair dye compositions of Examples 17 to 21 were excellent all in stability of the composition, dyeability and a feel during rinsing of the composition. In contrast, Comparative Example 6 was inferior in a feel during rinsing of the composition compared to Examples 17 to 21, and Comparative Example 7 was inferior all in stability of the composition, dyeability and a feel during rinsing of the composition compared to Examples 17 to 21.

TABLE 6

| | | Active amount (mass %) | Comparative Example | | Example | | | | |
|---|---|---|---|---|---|---|---|---|---|
| | | | 8 | 9 | 22 | 23 | 24 | 25 | 26 |
| First agent | (A) | Azo dye (A-2) | 0.5 | 0.5 | 0.5 | 0.5 | 0.5 | 0.5 | 0.5 |
| | (B2) | Steartrimonium chloride | — | 0.5 | 0.5 | 0.5 | 0.5 | 0.5 | 0.5 |
| | (C) | Sodium chloride | — | — | 1 | — | — | 0.5 | 2 |
| | | Potassium chloride | — | — | — | 1 | — | — | — |
| | | Sodium sulfate | — | — | — | — | 1 | — | — |
| | | Monoethanol amine | 1.5 | 1.5 | 1.5 | 1.5 | 1.5 | 1.5 | 1.5 |
| | | Water | Balance | Balance | Balance | Balance | Balance | Balance | Balance |
| | | Total | 100 | 100 | 100 | 100 | 100 | 100 | 100 |
| Second agent | | Hydrogen peroxide | 5.7 | 5.7 | 5.7 | 5.7 | 5.7 | 5.7 | 5.7 |
| | | Etidronic acid | 0.07 | 0.07 | 0.07 | 0.07 | 0.07 | 0.07 | 0.07 |
| | | Water | Balance | Balance | Balance | Balance | Balance | Balance | Balance |
| | | Total | 100 | 100 | 100 | 100 | 100 | 100 | 100 |
| | | (B2)/[(A) + (C)] mass ratio | 0 | 1.0 | 0.33 | 0.33 | 0.33 | 0.50 | 0.20 |
| | | (B)/[(A) + (C)] molar ratio | 0 | 1.06 | 0.08 | 0.10 | 0.17 | 0.15 | 0.04 |
| | | (A)/(B) molar ratio | — | 0.94 | 0.94 | 0.94 | 0.94 | 0.94 | 0.94 |
| | | pH (25° C.) | 9.9 | 9.8 | 9.8 | 9.8 | 9.8 | 9.8 | 9.8 |
| Evaluation | | Stability of composition | 3 | 1 | 3 | 3 | 3 | 3 | 3 |
| | | Dyeability (ΔE) | 54.3 | 49.9 | 56.7 | 57.5 | 58 | 56.5 | 55.5 |
| | | Feel (combing force; g) during rinsing of composition | 257.8 | 202.6 | 191.2 | 193.8 | 195.2 | 205.6 | 193 |

Based on the evaluation results of the stability of the first agent shown in Table 5 and the evaluation results shown in Table 6, the hair dye compositions of Examples 22 to 26 were excellent all in dyeability and a feel during rinsing of the composition. In contrast, Comparative Example 8 was inferior in a feel during rinsing of the composition compared to Examples 22 to 26, and Comparative Example 9 was inferior in dyeability compared to Examples 22 to 26.

Example 27 and Comparative Example 10

Hair dye compositions (one-agent type hair dye) having the compositions shown in Table 7 were prepared by the following method. The obtained hair dye compositions were evaluated for stability of a composition, dyeability and a feel during rinsing of a composition in the same manner as above. The evaluation results of these are all together shown in Table 7.

<Method for Preparing Hair Dye Composition>

In water, ammonium chloride and a component (C) were blended. After confirming dissolution of them, a component (B) was added. The mixture was stirred for a predetermined time to prepare Mixture 1. Separately, ammonia and components (A-1) to (A-3) were dissolved in water to prepare Mixture 2. Subsequently, Mixture 2 was blended with Mixture 1 and the resultant mixture was stirred for a predetermined time to obtain a hair dye composition.

TABLE 7

| | Active amount (mass %) | Comparative Example 10 | Example 27 |
|---|---|---|---|
| (A) | Azo dye (A-1) | 0.25 | 0.25 |
| (A) | Azo dye (A-2) | 0.15 | 0.15 |
| (A) | Azo dye (A-3) | 0.25 | 0.25 |
| (B2) | Cetrimonium chloride | 1.2 | 1.2 |
| (C) | Potassium chloride | — | 1 |
| | Ammonium chloride | 0.5 | 0.5 |
| | Ammonia | 1.76 | 1.76 |
| | Water | Balance | Balance |
| | Total | 100 | 100 |
| | (B2)/[(A) + (C)] mass ratio | 1.85 | 0.73 |
| | (B)/[(A) + (C)] molar ratio | 1.61 | 0.24 |

TABLE 7-continued

| | Active amount (mass %) | Comparative Example 10 | Example 27 |
|---|---|---|---|
| | (A)/(B) molar ratio | 0.62 | 0.62 |
| | pH (25° C.) | 10.4 | 10.4 |
| Evaluation | Stability of composition | 1 | 3 |
| | Dyeability (ΔE) | 22.9 | 25.2 |
| | Feel (combing force; g) during rinsing of composition | 217 | 191 |

As shown in Table 7, the hair dye composition of Example 27 was excellent all in stability of the composition, dyeability and a feel during rinsing of the composition. In contrast, Comparative Example 10 was inferior all in stability of composition, dyeability and a feel during rinsing of the composition, compared to Example 27.

Examples 28 to 33

Hair dye compositions (one-agent type hair dye) having the compositions shown in Table 8 were prepared by the following method. The obtained hair dye compositions were evaluated for dyeability and the presence or absence of precipitates during blending. The evaluation results are all together shown in Table 8.

<Method for Preparing Hair Dye Composition>

In water, ammonium chloride, alkyl glucosides and component (C) were blended. After confirming dissolution of them, a component (B) was added. The mixture was stirred for a predetermined time to prepare Mixture 1. Separately, ammonia and a component (A-2) were dissolved in water to prepare Mixture 2. Subsequently, Mixture 2 was blended with Mixture 1 and the resultant mixture was stirred for a predetermined time to obtain a hair dye composition.

TABLE 8

|  |  | Example | | | | | |
|---|---|---|---|---|---|---|---|
| | Active amount (mass %) | 28 | 29 | 30 | 31 | 32 | 33 |
| (A) | Azo dye (A-2) | 0.05 | 0.05 | 0.05 | 0.05 | 0.05 | 0.05 |
| (B2) | Cetyl trimethyl ammonium chloride*1 | 0.3 | 0.3 | 0.3 | 0.3 | 0.3 | 0.3 |
| | Lauryl trimethyl ammonium chloride*2 | 0.14 | 0.14 | 0.14 | 0.14 | 0.14 | 0.14 |
| (C) | Sodium bicarbonate | 0.05 | 0.5 | 1 | 2.5 | 5 | 7.5 |
| | Ammonium chloride | 0.5 | 0.5 | 0.5 | 0.5 | 0.5 | 0.5 |
| | Ammonia | 1.76 | 1.76 | 1.76 | 1.76 | 1.76 | 1.76 |
| | Alkyl glucoside *3 | 3 | 3 | 3 | 3 | 3 | 3 |
| | Water | Balance | Balance | Balance | Balance | Balance | Balance |
| | Total | 100 | 100 | 100 | 100 | 100 | 100 |
| | (B2)/[(A) + (C)] mass ratio | 4.40 | 0.80 | 0.42 | 0.17 | 0.09 | 0.06 |
| | (B)/[(A) + (C)] molar ratio | 2.01 | 0.24 | 0.12 | 0.05 | 0.03 | 0.02 |
| | (A)/(B) molar ratio | 0.09 | 0.09 | 0.09 | 0.09 | 0.09 | 0.09 |
| | pH (25° C.) | 10.39 | 10.39 | 10.38 | 10.38 | 10.36 | 10.36 |
| Evaluation | Dyeability | 20.3 | 24.2 | 26.5 | 24.6 | 23.1 | 21.8 |
| | Stability of composition | 2 | 3 | 3 | 3 | 3 | 2 |

*1 QUARTAMIN 60W, manufactured by Kao Corp.
*2 QUARTAMIN 24P, manufactured by Kao Corp.
*3 Mydol 10, manufactured by Kao Corp.

The invention claimed is:

1. A hair dye composition comprising the following components (A), (B) and (C) and having pH (25° C.) of 7.5 or more and 12 or less:

(A): one or more azo dyes selected from the group consisting of the following (A-1), (A-2) and (A-3):

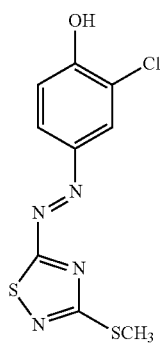

(A-1)

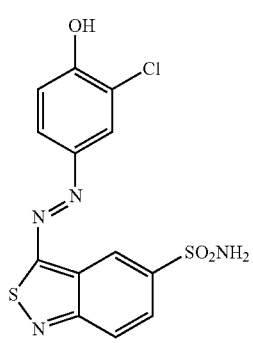

(A-2)

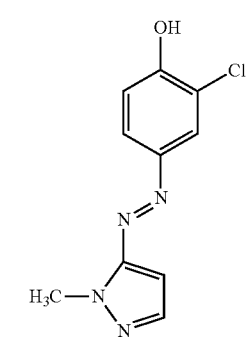

(A-3)

(B): a diallyl quaternized ammonium salt polymer derivative (C): 0.1 mass % or more and 8 mass % or less of at least one alkali metal salt of an acid selected from the group consisting of hydrochloric acid, carbonic acid and sulfuric acid, wherein the molar ratio of a whole component (B) relative to the total of a component (A) and a component (C) in a whole composition, (B)/[(A)+(C)] is from 0.08 to 2.00.

2. The hair dye composition according to claim 1, wherein the molar ratio of a whole component (B) relative to the total of a component (A) and a component (C) in a whole composition, (B)/[(A)+(C)], is 0.08 to 1.5.

3. The hair dye composition according to claim 1, wherein the component (B) is one or more member selected from the group consisting of dimethyl diallyl ammonium chloride polymer, a dimethyl diallyl ammonium chloride/acrylic acid copolymer, a dimethyl diallyl ammonium chloride/acrylamide copolymer, a dimethyl diallyl ammonium chloride/acrylic acid/acrylamide polymer, and hydroxyethylcellulose/dimethyl diallyl ammonium chloride copolymer.

4. The hair dye composition according to claim 1, wherein a nitrogen content in the component (B) is 0.3 mass % or more and 9.0 mass % or less.

5. The hair dye composition according to claim 1, wherein a content of the component (B) is 0.01 mass % or more and 10 mass % or less of a whole composition.

6. The hair dye composition according to claim 1, wherein a content of component (C) is 0.2 mass % or more and 7 mass % or less of the whole composition.

7. The hair dye composition according to claim 1, further comprising an anionic surfactant (D1) or a nonionic surfactant (D2) as a component (D).

8. The hair dye composition according to claim 7, wherein the component (D) is one or more member selected from the group consisting of an alkyl sulfate salt, a polyoxyalkylene alkyl sulfate salt, a fatty acid salt, an alkyl ether carboxylate salt, an alkyl glyceryl ether, and an alkyl polyglucoside.

9. The hair dye composition according to claim 7, wherein a content of the component (D) is 0.1 mass % or more and 20 mass % or less of the whole composition.

10. The hair dye composition according to claim 1, further comprising an alkali agent as a component (E) in an amount of 0.01 mass % or more and 20 mass % or less of the whole composition.

11. A hair dye composition comprising the following components (A), (B) and (C) and having pH (25° C.) of 7.5 or more and 12 or less:

(A): one or more azo dyes selected from the group consisting of the following (A-1), (A-2) and (A-3):

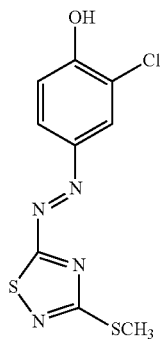
(A-1)

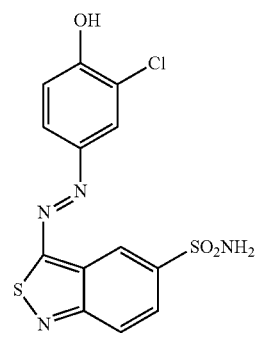
(A-2)

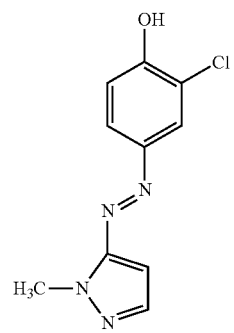
(A-3)

(B): a diallyl quaternized ammonium salt polymer derivative (C): 0.1 mass % or more and 8 mass % or less of at least one alkali metal salt of an acid selected from the group consisting of hydrochloric acid and sulfuric acid.

12. The hair dye composition according to claim 11, wherein the component (C) is one or more member selected from the group consisting of sodium chloride, potassium chloride, sodium sulfate, and potassium sulfate.

13. A method for dyeing hair, comprising:
applying the hair dye composition according to claim 1 to the hair, allowing to stand for 1 to 60 minutes, and washing away the composition.

* * * * *

UNITED STATES PATENT AND TRADEMARK OFFICE
CERTIFICATE OF CORRECTION

PATENT NO.         : 10,470,990 B2
APPLICATION NO.    : 15/316291
DATED              : November 12, 2019
INVENTOR(S)        : Hiromi Saimiya et al.

Page 1 of 1

It is certified that error appears in the above-identified patent and that said Letters Patent is hereby corrected as shown below:

On the Title Page

Item (71), the Applicant's city is incorrect. Item (71) should read:
--(71) Applicant: KAO CORPORATION, Tokyo (JP)--

Item (87), the PCT Publication Number is incorrect. Item (87) should read:
--(87) PCT Pub. No.: WO2015/186815
      PCT Pub. Date: Dec. 10, 2015--

Signed and Sealed this
Twenty-eighth Day of January, 2020

Andrei Iancu
*Director of the United States Patent and Trademark Office*